United States Patent [19]
Markkula et al.

[11] Patent Number: 6,056,976
[45] Date of Patent: *May 2, 2000

[54] ELASTOMER, ITS PREPARATION AND USE

[75] Inventors: Tommi Markkula; Juha Ala-Sorvari; Harri Jukarainen, all of Turku, Finland; Matti Lehtinen, Piispanristi; Jarkko Rughonen, Vanhalinna, all of Finland

[73] Assignee: Leiras Oy, Turku, Finland

[ * ] Notice: This patent issued on a continued prosecution application filed under 37 CFR 1.53(d), and is subject to the twenty year patent term provisions of 35 U.S.C. 154(a)(2).

[21] Appl. No.: 09/190,608

[22] Filed: Nov. 12, 1998

[51] Int. Cl.$^7$ ........................................................ A61K 9/14
[52] U.S. Cl. ........................... 424/486; 528/15; 524/588; 424/484
[58] Field of Search .................................. 528/15, 24, 42; 524/588; 424/484, 486

[56] References Cited

U.S. PATENT DOCUMENTS

| | | | |
|---|---|---|---|
| 3,050,492 | 8/1962 | Polmanteer et al. | 528/24 |
| 3,179,619 | 4/1965 | Brown | 528/42 |
| 3,854,480 | 12/1974 | Zaffaroni | 128/260 |
| 5,492,993 | 2/1996 | Saam et al. | 528/42 |
| 5,733,569 | 3/1998 | Moo-Young et al. | 424/424 |
| 5,824,736 | 10/1998 | Kobayashi et al. | 514/588 |

*Primary Examiner*—Thurman K. Page
*Assistant Examiner*—Amy E Pulliam
*Attorney, Agent, or Firm*—Lydon & Brown, LLP

[57] ABSTRACT

The invention relates to a siloxane-based elastomer intended for controlling the permeation of drugs, wherein the elastomer includes 3,3,3,-trifluoropropyl groups attached to the Si-atoms of the siloxane units.

The invention relates also to a method for the preparation of a siloxane-based elastomer including 3,3,3,-trifluoropropyl substituents, where the elastomer is intended for controlling the permeation of drugs.

In the method either i) a 3,3,3,-trifluoropropyl-substituted vinyl-functional polysiloxane component and a silicon hydride-functional crosslinking agent are crosslinked in the presence of a catalyst, or ii) a 3,3,3,-trifluoropropyl-substituted polysiloxane component is crosslinked in the presence of a peroxide catalyst.

5 Claims, No Drawings

ELASTOMER, ITS PREPARATION AND USE

FIELD OF THE INVENTION

This invention relates a siloxane-based elastomer intended for controlling the permeation of drugs, and to & method for the preparation thereof.

BACKGROUND OF THE INVENTION

The publications and other materials used herein to illuminate the background of the invention, and in particular, the cases to provide additional details respecting the practice, are incorporated by reference.

Polysiloxanes, such as poly(dimethylsiloxane) (PDMS), are highly suitable for use as a membrane or a matrix regulating the permeation of drugs in various drug forms, in particular in implants and IU systems. Polysiloxanes are physiologically inert, and a wide group of drugs are capable of penetrating polysiloxane membranes, which also have the required mechanical properties.

It is known from the literature that the adding of poly (ethylene oxide) groups, i.e. PEO groups, to a PDMS polymer may increase the permeation of drugs. Publication KL Ullmann et al., Journal of Controlled Release 10 (1989) 251–260, describes membranes prepared from a block copolymer which contains PEO and PDMS and the penetration of various steroids through these membranes. It is further known that membranes based on modified PDMS polymers, in which a certain amount of the methyl substituents at the Si-atoms are replaced by trifluoropropyl groups, decrease the permeation of drugs. The publication Ying Sun et al., Journal of Controlled Release, 5 (1987) 69–78, describes the effect on membranes prepared from PDMS, trifluoropropyl substituted PDMS and PDMS/PEO/PMMA (where PMMA is poly(methylmethacrylate)) on the permeation of androgenic and progestanic steroids. The study shows that the permeation for both groups of steroids was lower for the membrane made of trifluoropropyl substituted PDMS than for that made of unmodified PDMS. The publication did not, however, disclose any elastomer made of trifluoropropyl substituted PDMS.

OBJECTS OF THE INVENTION

The object of the invention is to provide an elastomer which is easy to prepare, through which a drug permeates at a desired rate, and which gives the membrane the required mechanical properties.

The object of the invention is in particular to provide an elastomer through which the permeation of drugs with hormonal action can be controlled.

A particularly important object of this invention is to provide an elastomer which retards the drug permeation in comparison with elastomers of normal PDMS.

SUMMARY OF THE INVENTION

The invention relates to a siloxane-based elastomer intended for controlling the permeation of drugs. The elastomer is characterized in that it comprises 3,3,3,-trifluoropropyl groups attached to the Si-atoms of the siloxane units.

Furthermore, the invention relates to a method for the preparation of a siloxane-based elastomer comprising 3,3,3,-trifluoropropyl substituents, wherein said elastomer is intended for controlling the permeation of drugs. The method is characterized in that either i) a 3,3,3-trifluoropropyl-substituted vinyl-functional polysiloxane component and a silicon hydride-functional crosslinking agent are crosslinked in the presence of a catalyst, or ii) a 3,3,3-trifluoropropyl-substituted polysiloxane component is crosslinked in the presence of a peroxide catalyst.

DETAILED DESCRIPTION OF THE INVENTION

General description of the novel elastomer

The term "siloxane-based elastomer" shall be understood to cover elastomers made of poly(disubstituted siloxanes) where the substituents mainly are lower alkyl, preferably alkyl groups of 1 to 6 carbon atoms, or phenyl groups, wherein said alkyl or phenyl can be substituted or unsubstituted. A widely used and preferred polymer of this kind is poly(dimethylsiloxane) or PDMS.

According to the invention, a certain amount of the substituents attached to the Si-atoms of the siloxane units in the elastomer shall be 3,3,3,-trifluoropropyl groups. Such an elastomer can be achieved in different ways. According to one embodiment, the elastomer can be based on one single crosslinked siloxane-based polymer, such as a poly(dialkyl siloxane) where a certain amount of the alkyl groups at the Si-atoms are replaced by 3,3,3-trifluoropropyl groups. A preferred example of such polymers is poly(3,3,3-trifluoropropyl methyl siloxane) the structure of which is shown as compound I below.

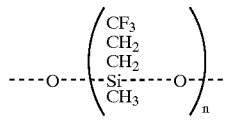

Compound I

A polymer of this kind, in which approximately 50% of the methyl substituents at the Si-atoms replaced by 3,3,3-trifluoropropyl groups, is commercially available. The term "approximately 50%" means that the degree of 3,3,3-trifluoropropyl substitution is in fact somewhat below 50%, because the polymer must contain a certain amount (about 0.15% of the substituents) of crosslinkable groups such as vinyl or vinyl-terminated groups. Similar polymers having lower substitution degree of 3,3,3-trifluoropropyl groups can easily be synthetized.

The retarding effect of the 3,3,3-trifluoropropyl groups on the permeation of drugs across a membrane of the elastomer is dependent on the amount of these groups. Furthermore, the effect is highly dependent on the drug used. If the elastomer is made of one single polymer only, it would be necessary to prepare and use polymers with different amounts of 3,3,3,-trifluoropropyl groups for different drugs.

According to another embodiment, which is particularly preferred if suitable elastomers for several different drugs are needed, is to crosslink a mixture comprising a) a non-fluorosubstituted siloxane-based polymer and b) a fluorosubstituted siloxane-based polymer, where said polymer comprises 3,3,3,-trifluoropropyl groups attached to the Si-atoms of the siloxane units. The first ingredient of the mixture, the non-fluorosubstituted polymer, can be any poly(disubstituted siloxane) where the substituents mainly are lower alkyl, preferably alkyl groups of 1 to 6 carbon atoms, or phenyl groups, wherein said alkyl or phenyl can be substituted or unsubstituted. A preferred non-fluorosubstituted polymer is PDMS. The second ingredient of the mixture, the fluoro-substituted polymer, can for example be a poly(dialkyl siloxane) where a certain amount of the alkyl groups at the Si-atoms are replaced by 3,3,3-trifluoropropyl groups. A preferred example of such polymers is poly(3,3,3-trifluoropropyl methyl siloxane) as mentioned above. A particularly preferable polymer of this kind is a polymer having as high amount of 3,3,3,-trifluoropropyl substituents as possible, such as the commercially available polymer, in which approximately 50% of the methyl substituents at the Si-atoms are replaced by 3,3,3-trifluoropropyl groups. An elastomer with great permeation retarding effect can be achieved by using exclusively or mainly the aforementioned polymer. Elastomers with less retarding influence on the permeation of the drug can be obtained by using mixtures with increasing amounts of the non-fluorosubstituted siloxane-based polymer.

The elastomer should preferably comprise a filler, such as amorphous silica, in order to give a sufficient strength for the membrane made from said elastomer.

General description of the method for the preparation of the elastomer

According to one embodiment, the novel elastomer is prepared by crosslinking, in the presence of a catalyst, a vinyl-functional polysiloxane component and a silicon hydride-functional crosslinking agent.

By crosslinking in meant the addition reaction of the silicon hydride-functional crosslinking agent with the carbon-carbon double bond of the vinyl-functional polysiloxane component.

According to another embodiment, the elastomer is prepared by crosslinking the polymer In the presence of a peroxide catalyst.

The term "vinyl-functional" polysiloxane shall be understood to cover polysiloxanes substituted with vinyl groups or with vinyl-terminated groups. The "vinyl-functional polysiloxane component" and the "polysiloxane component" to be crosslinked shall also be understood to cover copolymers with polysiloxanes having vinyl substituents or vinylterminated substituents. For crosslinking, the amounts of the components are preferably selected so that the ratio of the molar amounts of the silicon hydrides to the double bonds is at least 1.

As stated above, the elastomer according to this invention can be made by crosslinking one single fluorosubstituted siloxane-based polymer, or by crosslinking a mixture of a non-fluorosubstituted siloxane-based polymer and a fluorosubstituted siloxane-baaed polymer. The term "vinyl-functional polysiloxane component" can thus be a mixture comprising a non-fluorosubstituted siloxane-based polymer and a fluorosubstituted siloxane-based polymer, where said polymer comprises 3,3,3,-trifluoropropyl groups attached to the Si-atoms of the siloxane units. Alternatively, the "vinyl-functional polysiloxane component" can be a single fluoro-substituted siloxane-based polymer, where said polymer comprises 3,3,3,-trifluoropropyl groups attached to the Si-atoms of the siloxane units.

The silicon hydride-functional crosslinking agent is preferably a hydride-functional polysiloxane which may be straight-chain, branched or cyclic.

The fluorosubstituted siloxane-based polymer is preferably a PDMS polymer where approximately 50% of the methyl groups in said PDMS have been replaced by 3,3,3,-trifluoropropyl groups.

A filler, such as amorphous silica, is preferably added to the vinyl-functional component before the crosslinking.

In case the elastomer is made by crosslinking a polymer component in the presence of a peroxide catalyst, such a polymer component can be a mixture comprising a non-fluorosubstituted siloxane-based polymer and a fluorosubstituted siloxane-based polymer comprising 3,3,3,-trifluoropropyl groups attached to the Si-atoms of the siloxane units. Alternatively, this polymer component can be a single fluorosubstituted siloxane-based polymers where said polymer comprises 3,3,3,-trifluoropropyl groups attached to the Si-atoms of the siloxane units.

The catalyst to be used in the crosslinking is preferably a noble metal catalyst, most commonly a platinum complex in alcohol, xylene, divinyl siloxane or cyclic vinyl siloxane. An especially suitable catalyst is a Pt(O)-divinyl-tetramethyl disiloxane complex.

EXPERIMENTAL SECTION

The invention is described below in greater detail in the following examples.

Elastomers of different types (A–E) were prepared. Type A represents an elastomer made from a mixture comprising fluorosubstituted (3,3,3-trifluoropropyl substitution degree 49.5%) and non-fluorosubstituted siloxane-based polymers wherein the crosslinking was performed by peroxide catalyst. Three different mixtures with varying amounts of fluorosubstituted polymer were prepared (Example 1). The B type (Examples 2 and 3) represents and elastomer made from a single fluorosubstituted siloxane-based polymer wherein the crosslinking was performed by peroxide catalyst. Type C (Example 4) represents an elastomer made from a mixture comprising fluorosubstituted (3,3,3-trifluoropropyl substitution degree 49.5%) and non-fluorosubstituted siloxane-based polymers wherein the crosslinking was performed by peroxide catalyst. The D type (Example 5) represents an elastomer made from a single fluorosubstituted siloxane-based polymer wherein the crosslinking was performed by hydrosilylation. Type E (Example 6) represents an elastomer made from a mixture comprising fluorosubstituted (3,3,3-trifluoropropyl substitution degree 30%) and non-fluorosubstituted siloxane-based polymers wherein the crosslinking was performed by hydrosilylation,

EXAMPLE 1

Type A elastomers with varying amounts fluorosubstituted polymers

A series of 50 [and further 25 and 75] parts by weight of silica-filled poly(trifluoropropylmethylsiloxane-co-vinylmethylsiloxane), 50 [and 75 and 25 respectively] parts by weight of silica-filled poly(dimethylsiloxane-co-vinylmethylsiloxane) and 1.2 parts by weight of dibentsoylperoxide-polydimethylsiloxane paste were mixed with a 2-roll mill. The mixture was cured at +115° C. for 5 minutes with a thermal press to give 0.4 mm thick membranes, which were post-cured at +150° C. for 2 hours.

EXAMPLE 2

Elastomer type B 100 parts by weight of silica-filled poly(trifluoropropylmethylsiloxane-co-dimethylsiloxane-co-vinylmethylsiloxane) (content of trifluoropropylmethyl-siloxane units 60 mol-%; i.e. degree of trifluoropropyl substitution groups is 30%) and 1.2 parts by weight of dibentsoylperoxide-polydimethylsiloxane paste were mixed with a 2-roll mill. The mixture was cured at +115° C. for 5 minutes with a thermal press to give 0.4 mm thick membranes, which were post-cured at +150° C. for 2 hours.

EXAMPLE 3

Elastomer type B 100 parts by weight of silica-filled poly(trifluoropropylmethylsiloxane-co-dimethylsiloxane-co-vinylmethylsiloxane) (content of trifluoropropylmethylsiloxane units 99 mol-%; i.e. degree of trifluoropropyl substitution 49.5%) and 1.2 parts by weight of dibentsoylperoxide-polydimethylsiloxane paste were mixed with a 2-roll mill. The mixture was cured at +115° C. for 5 minutes with a thermal press to give 0.4 mm thick membranes, which were post-cured at +150° C. for 2 hours.

EXAMPLE 4

Elastomer type C 50 parts by weight of the silica-filled fluoro-substituted polysiloxane in Example 2, 50 parts by weight of silica-filled poly(dimethylsiloxane-co-vinylmethylsiloxane) and 1.2 parts by weight of dibentsoylperoxide-polydimethylsiloxane paste were mixed with a 2-roll mill. The mixture was cured at +115° C. for 5 minutes with a thermal press to give 0.4 mm thick membranes, which were post-cured at +150° C. for 2 hours.

EXAMPLE 5

Elastomer type D 100 parts by weight of silica-filled poly(trifluoropropylmethylsiloxane-co-vinylmethylsiloxane) (substitution degree of 3,3,3-trifluoropropyl groups=49.5%), 0.04 parts by weight of Pt(O)-divinyltetramethylsiloxane complex, 0.05 parts by weight of 1-ethinyl-1-cyclohexanol and 1.0 parts by weight of silicon hydride crosslinking agent were mixed with a two-chamber mixer. The mixture was cured at +115° C. for 5 minutes with a thermal press to give 0.4 mm thick membranes.

EXAMPLE 6

Elastomer type E 50 parts by weight of the silica-filled fluoro-substituted polysiloxane in Example 5, 50 parts by weight of silica-filled poly(dimethylsiloxane-co-vinylmethylsiloxane), 0.04 parts by weight of Pt(O)-divinyltetramethylsiloxane complex, 0.05 parts by weight of 1-ethinyl-1-cyclohexanol and 1.0 parts by weight of silicon hydride crosslinking agent were mixed with a two-chamber mixer. The mixture was cured at +115° C. for 5 minutes with a thermal press to give 0.4 mm thick membranes.

Membrane permeation studies

The permeation of different drugs through elastomers of types A, B and C described above were tested.

The test apparatus described in the publication Yie W. Chien, Transdermal Controlled Systemic Medications, Marcel Dekker inc. New York and Basel 1987, page 173, was used in the permeation tests.

The drug fluxes (permeations) through membranes were measured with a two-compartment diffusion cell at 37° C. (side-by-side diffusion cell, Crown Glass Company). The apparatus consisted of two concentric cells (donor and receptor compartments) that were separated by the elastomer membrane to be investigated. The donor and receptor compartments were both jacketed and thermostated by an external circulating bath and each compartment had a magnetic stirrer. A drug solution and solvent (without drug) was added into the donor and the receptor compartments. At each predetermined time interval, samples were withdrawn from the receptor compartment and replaced with the same volume of solvent. The amount of the drug that permeated through the membrane was measured by HPLC. In all measurements, the thickness (0.4 mm) of the membrane and the surface area of the membranes were constant.

In the following tables, the relative permeation through different elastomers were studied for different drugs. The reference elastomer is dimethylsiloxane-vinylmethylsiloxane copolymer, which contains silica filler. In the tables below, the term "trifluoropropyl substitution degree, %" has the same meaning as mentioned before and this percentage means the substituents at the Si-atoms of the siloxane units in the elastomer, i.e. the 3,3,3-trifluoropropyl substituents.

| Drug 1: Gestodene | | |
|---|---|---|
| Elastomer type | trifluoropropyl substitution degree, % | Relative permeation |
| reference | 0 | 1 |
| A | 7 | 0.63 |
| A | 16 | 0.37 |
| A | 29.5 | 0.18 |
| B | 30 | 0.45 |
| B | 49.5 | 0.06 |

| Drug 2: 17-β-estradiol | | |
|---|---|---|
| Elastomer type | trifluoropropyl substitution degree, % | Relative permeation |
| reference | 0 | 1 |
| B | 30 | 0.23 |
| B | 49.5 | 0.04 |

| Drug 3: Nestorone ™ (16-methylene-17-α-acetoxy-19-norprogesterone) | | |
|---|---|---|
| Elastomer type | trifluoropropyl substitution degree, % | Relative permeation |
| reference | 0 | 1 |
| B | 49.5 | 0.29 |

| Drug 4: MENT (7-α-methyl-19-nortestosterone) | | |
|---|---|---|
| Elastomer type | trifluoropropyl substitution degree, % | Relative permeation |
| reference | 0 | 1 |
| B | 49.3 | 0.09 |

| Drug 5: MENT Ac (7-α-methyl-19-nortestosterone acetate) | | |
|---|---|---|
| Elastomer type | trifluoropropyl substitution degree, % | Relative permeation |
| reference | 0 | 1 |
| A | 7 | 0.59 |
| A | 16 | 0.49 |
| A | 29.5 | 0.26 |
| B | 49.5 | 0.20 |

| Drug 6: Levonorgestrel | | |
|---|---|---|
| Elastomer type | trifluoropropyl substitution degree, % | Relative permeation |
| reference | 0 | 1 |
| B | 20 | 0.77 |
| B | 30 | 0.41 |
| B | 49.5 | 0.05 |
| C | 11 | 0.73 |

An elastomer according to the invention is, for example, highly suited for controlling, in implants and In intrauterine and intravaginal devices, the permeation of drugs having hormonal action.

The elastomer according to the invention is particularly suitable for the release of hormonally active drugs such as androgens, antiprogestins, progestins and estrogens.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

What is claimed is:

1. A method for controlling the permeation of a drug over a prolonged period of time by the use of a siloxane-based elastomer, comprising
   dispersing said drug within said siloxane-based elastomer to form a matrix or
   encasing said drug as a core within a membrane comprising said siloxane-based elastomer,
   wherein said elastomer comprises 3,3,3-trifluoropropyl groups attached to the Si-atoms of the siloxane units,
   wherein from 1 to approximately 50% of the substituents attached to the Si-atoms in the siloxane units are 3,3,3-trifluoropropyl groups, and
   wherein the elastomer is made of either
     (i) a mixture comprising (a) a non-fluorosubstituted siloxane-based polymer and (b) a fluorosubstituted siloxane-based polymer, said polymer comprising 3,3,3-trifluoropropyl groups attached to the Si-atoms of the siloxane units, or
     (ii) a single siloxane-based polymer comprising 3,3,3-trifluoropropyl groups attached to the Si-atoms of the siloxane units,
   wherein said polymer or mixture of polymers is crosslinked to form the elastomer.

2. The method of claim 1, wherein the mixture of polymers is a mixture of (a) poly(dimethylsiloxane) and (b) poly(dimethylsiloxane) in which at least 30% of the methyl groups attached to the Si-atoms of the siloxane units have been replaced by 3,3,3-trifluoropropyl groups.

3. The method of claim 2, wherein approximately 50% of the methyl groups in the polymer (b) have been replaced by 3,3,3-trifluoropropyl groups.

4. The method of claim 1, wherein said elastomer contains a filler.

5. The method of claim 4, wherein said filler comprises amorphous silica.

* * * * *

UNITED STATES PATENT AND TRADEMARK OFFICE
CERTIFICATE OF CORRECTION

PATENT NO. : 6,056,976
DATED : May 2, 2000
INVENTOR(S) : Tommi Markkula, Juha Ala-Sorvari, Harri Jukarainen, Matti Lehtinen and Jarkko Ruohonen It is certified that error appears in the above-indentified patent and that said Letters Patent is hereby corrected as shown below:

On the cover page, the name of the fifth inventor should appear as follows: Jarkko Ruohonen Signed and Sealed this Sixth Day of March, 2001

*Attest:*

NICHOLAS P. GODICI

*Attesting Officer*  Acting Director of the United States Patent and Trademark Office